(12) United States Patent
Messerli

(10) Patent No.: US 6,290,192 B1
(45) Date of Patent: Sep. 18, 2001

(54) ADJUSTABLE RECEIVER TUBE

(76) Inventor: Loyd R. Messerli, 4907 S. 90th St., Omaha, NE (US) 68127

( * ) Notice: Subject to any disclaimer, the term of this patent is extended or adjusted under 35 U.S.C. 154(b) by 0 days.

(21) Appl. No.: 09/501,203

(22) Filed: Feb. 10, 2000

Related U.S. Application Data

(60) Provisional application No. 60/122,375, filed on Mar. 2, 1999.

(51) Int. Cl.[7] .............................. F16M 11/26; A47C 21/00
(52) U.S. Cl. ..................... 248/188.5; 248/413; 248/523; 403/104; 403/329; 403/362; 5/503.1
(58) Field of Search .................................. 248/407, 408, 248/413, 73, 125.1, 125.2, 125.8, 121, 122.1, 158, 230.1, 229.1, 316.2, 188.5, 311.3, 519, 523, 535; 403/109.3, 109.4, 109.5, 109.6, 362, 329, 108, 104; 5/503.1; 180/907

(56) References Cited

U.S. PATENT DOCUMENTS

| | | | |
|---|---|---|---|
| 1,970,624 | 8/1934 | Recker | 248/2 |
| 3,047,061 | * 7/1962 | Wilcox et al. | 160/351 |
| 3,167,292 | * 1/1965 | Meyerowitz | 248/230.1 |
| 3,604,734 | * 9/1971 | Friedman | 403/104 |
| 4,655,632 | * 4/1987 | Smith | 403/362 |
| 4,715,488 | * 12/1987 | Hewitt et al. | 193/35 R |
| 4,725,027 | 2/1988 | Bekanich | 248/125 |
| 5,039,043 | * 8/1991 | Hodge | 248/125 |
| 5,135,191 | 8/1992 | Schmuhl | 248/125 |
| 5,366,191 | 11/1994 | Bekanich | 248/125 |
| 5,458,427 | 10/1995 | Simond | 403/109 |

* cited by examiner

Primary Examiner—Ramon O Ramirez
Assistant Examiner—Jon Szumny
(74) Attorney, Agent, or Firm—Koley Jessen P.C., A Limited Liability Organization; Mark D. Frederiksen

(57) ABSTRACT

An adjustable receiver tube includes an elongated tube having a flat resilient strap extending within the tube from the upper end of the cylindrical side wall. A flange at the bottom of the tube will support an IV pole within the tube, and a threaded shaft threaded through an aperture in the side of the tube will move the strip into engagement with an IV pole to hold the pole snugly within the receiver tube. A cushion is preferably mounted in the tube on the flange, to frictionally engage the lower end of the IV pole and prevent rotation, horizontal movement, and prevent damage to the lower end of the IV pole.

19 Claims, 3 Drawing Sheets

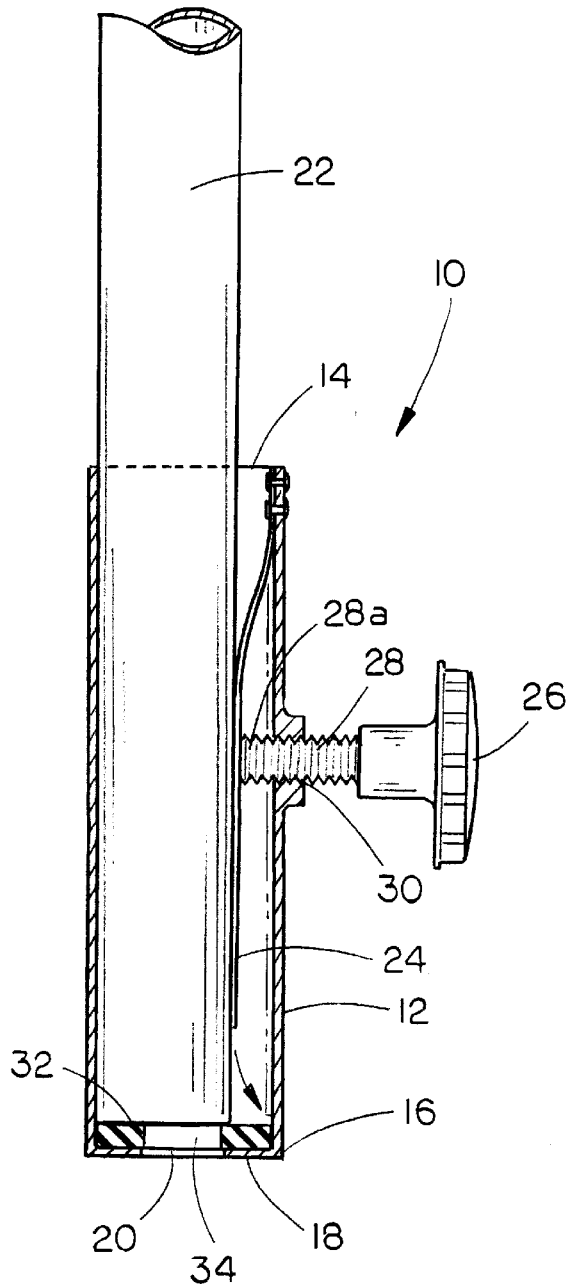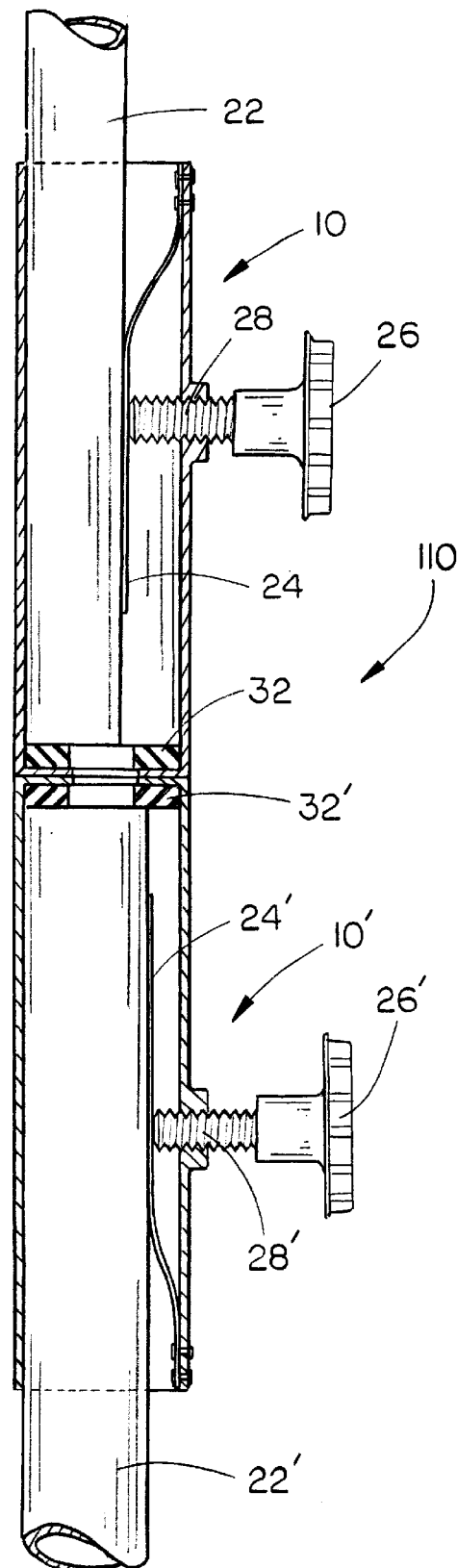
FIG. 1
FIG. 2

ADJUSTABLE RECEIVER TUBE

CROSS-REFERENCES TO RELATED APPLICATIONS

This application refers to and claims the benefit of the filing date of the U.S. provisional patent application Ser. No. 60/122,375, filed Mar. 2, 1999, entitled ADJUSTABLE RECEIVER TUBE.

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to poles utilized to transport intravenous fluid bags and pumps (IV poles and pumps), and more particularly to an improved receiver tube for receiving a variety of diameters of IV poles in at least one end for removable attachment to wheelchairs, beds, and other equipment, as well as other IV pole bases.

(2) Background Information

In the hospital environment, it is typically difficult, awkward, and inefficient to move a patient in a wheelchair along with an associated IV pole which supports one or more IV bags and pump. In some cases, it requires two people to accomplish such a task, one person pushing the wheelchair, and a second person moving the associated IV pole.

Another difficulty with conventional movement of a patient in a bed is the need to transfer the fusion pump and IV bag from one pole mounted on a bed to a second "transportable" pole having a wheeled base. Every time a patient is moved from a stationary location, such as a bed or a chair, a nurse or aid is needed for the transfer of the pump and IV bag, as well as the transport of the patient and IV pole.

Various prior art devices have been devised to alleviate some of these problems. For example, U.S. Pat. No. 4,725,027 to Joseph Bekanich discloses an IV equipment support with a removable upper section of an IV pole which may be journaled within a tube mounted on a gurney or the like. Similarly, U.S. Pat. No. 5,135,191 to James Schmuhl discloses a medical support system having an IV pole with an upper section which may be removed and journaled within a tube mounted on a gurney or wheelchair for supporting the IV pump and bag.

While both of the above-identified patents assist in making IV pumps and equipment more easily moved from one location to another, they both suffer the same problem. They require a specific diameter receiver tube to receive the IV pole upper half. Thus, the receiver tubes on the gurneys and wheelchairs must be matched in diameter to receive a specific IV pole. Because a wide variety of manufacturers may make gurneys, wheelchairs, and IV pole bases, this requirement effectively restricts the purchase of medical support systems to a single manufacturer of all components.

BRIEF SUMMARY OF THE INVENTION

It is therefore a general object of the present invention to provide an improved receiver tube for receiving and retaining a variety of diameters of IV poles within a single tube.

Another object is to provide an adjustable receiver tube which restrains rotational movement of the IV pole and horizontal movement of the lower end of the IV pole, within the receiver tube.

Still another object of the present invention is to provide a receiver tube which may interconnect upper and lower poles of different diameters.

Yet another object is to provide a receiver tube which is simple to operate and attach to an IV pole, and economical to manufacture.

These and other objects of the present invention will be apparent to those skilled in the art.

The adjustable receiver tube of the present invention includes an elongated tube having a flat resilient strap extending within the tube from the upper end of the cylindrical side wall. A flange at the bottom of the tube will support an IV pole within the tube, and a threaded shaft threaded through an aperture in the side of the tube will move the strip into engagement with an IV pole to hold the pole snugly within the receiver tube. A cushion is preferably mounted in the tube on the flange, to frictionally engage the lower end of the IV pole and prevent rotation, horizontal movement, and prevent damage to the lower end of the IV pole.

BRIEF DESCRIPTION OF THE SEVERAL VIEWS OF THE DRAWING

The preferred embodiments of the invention are illustrated in the accompanying drawings, in which similar or corresponding parts are identified with the same reference numeral throughout the several views, and in which:

FIG. 1 is a vertical sectional view taken through the receiver tube of the present invention;

FIG. 2 is a vertical sectional view through a second embodiment of the receiver tube;

DETAILED DESCRIPTION OF THE INVENTION

Figure 3:
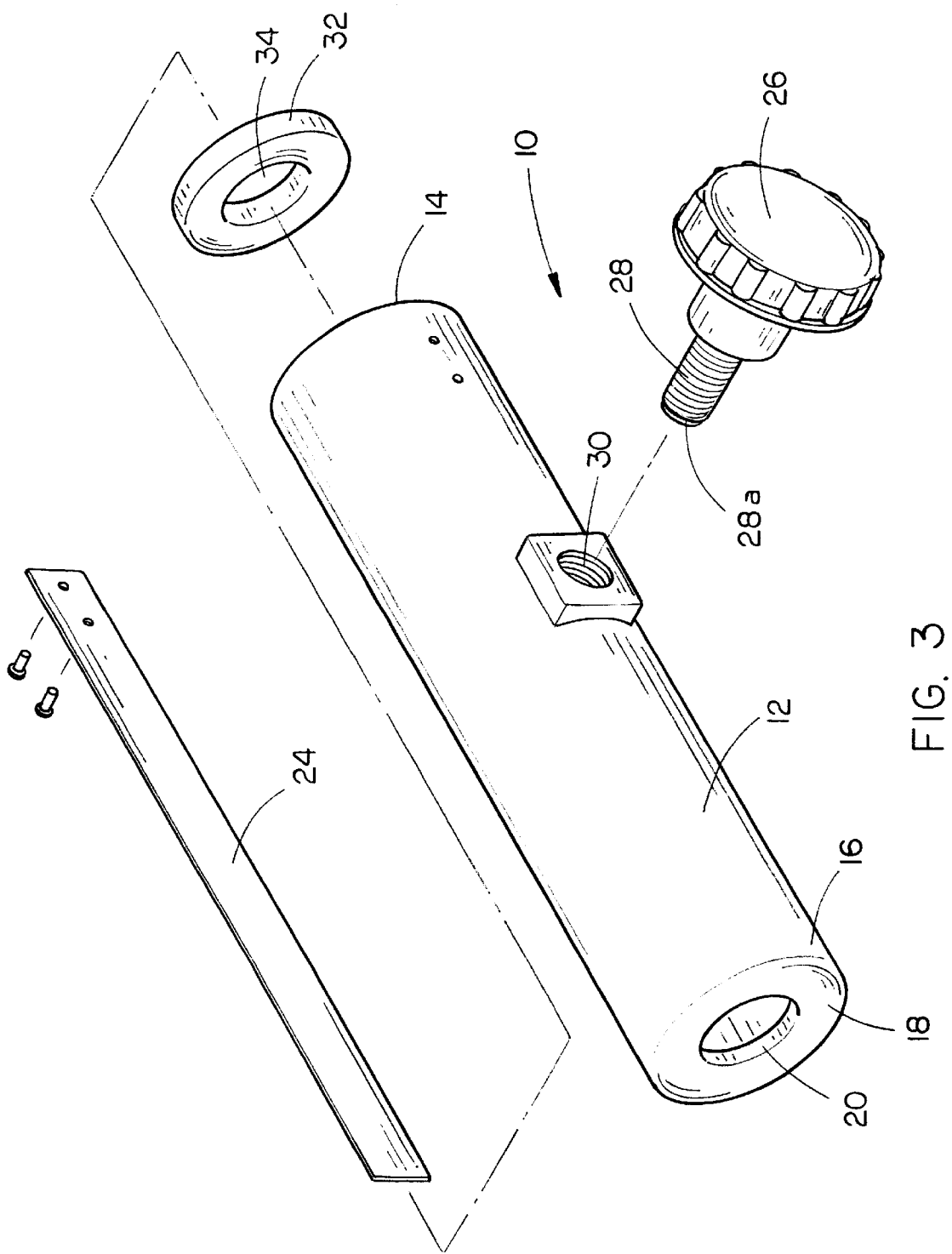
FIG. 3 is an exploded perspective view of the receiver tube shown in FIG. 1.

Referring now to the drawings, and more particularly to FIG. 1, the receiver tube of the present invention is designated generally at 10 and includes a generally hollow cylindrical tube 12 having an open upper end 14 and a lower end 16. An annular flange 18 is mounted in the lower end 16 of tube 12, with a central aperture 20 therethrough. Flange 18 forms a bottom within tube 12 upon which an upper pole 22 is supported. Aperture 20 prevents the buildup of pressure within receiver tube 10, as pole 22 is inserted therein. In addition, fluids are quickly and easily drained from the receiver tube, to prevent rust, bacteria, or other related problems.

A flat guide strip 24 of spring steel forms a guide to direct pole 22 against one interior surface of tube 12 as the pole is journaled within the tube. Guide strip 24 is fastened to an interior surface of tube 12 at the upper end 14 thereof, and extends downwardly towards flange 18.

An adjustment knob 26 is mounted on a threaded shaft 28 to selectively rotate shaft 28 through threaded aperture 30 in the side wall of tube 12. Aperture 30 is located in alignment with guide strip 24, such that the inward end 28a of shaft 28 is moved into contact with guide strip 24 as knob 26 is rotated. Because guide strip 24 is formed of spring steel, it will return to a position flush against the interior wall of tube 12, as knob 26 is rotated to withdraw the inward end 28a of shaft 28 outwardly. In this position, a pole 22 having a diameter slightly less than the inner diameter of tube 12 may be received within receiver tube 10 and secured in position with knob 26 and shaft 28. For smaller diameter, poles, shaft 28 is threaded inwardly to push guide strip 24 into contact against the pole 22, and thereby secure pole 22 firmly against the interior side wall of tube 12 opposing aperture 30. Guide strip 24 also prevents damage to the surface of pole 22 by the inward end 28a of shaft 28.

A rubber ring-shaped cushion 32 is supported on the flange 18 and supports pole 22 on flange 18. The use of rubber, or similar material, for cushion 32 is desirable to frictionally engage the lower end of pole 22 and thereby resists any tendency of pole 22 to rotate within receiver tube 10. In addition, cushion 32 will prevent damage to the lower end of the IV pole, and also prevent horizontal movement of the lower end of the pole, thereby preventing any potential "wobble" which may occur between the point of contact of the threaded shaft 28 and the flange 18. Cushion 32 also has a central opening 34 therethrough aligned with aperture 20, to permit the flow of air and liquids into and out of receiver tube 10.

Referring now to FIG. 2, a second embodiment of the receiver tube is designated generally at 110 and is essentially a combination of two receiver tubes 10 of the first embodiment, connected together in coaxial alignment at their lower ends. Thus, an upright receiver tube 10 is coaxially mounted to an inverted receiver tube 10' to form the second embodiment of the receiver tube 110. Upright receiver tube 10 will thereby retain an upper pole 22 therein while lower receiver tube 10' will receive and retain a lower pole 22' of a diameter which may be different than upper pole 22. Each receiver tube 10 and 10' includes the same knob 26 and 26', shaft 28 and 28', and guide strip 24 and 24', as well as cushion 32 and 32'.

Although FIG. 2 shows a pair of receiver tubes 10 and 10' connected together to form receiver 110, receiver tube 110 could be a single elongated tube with a single flange mounted generally midway between the open ends to form the same unit.

Figure 4:
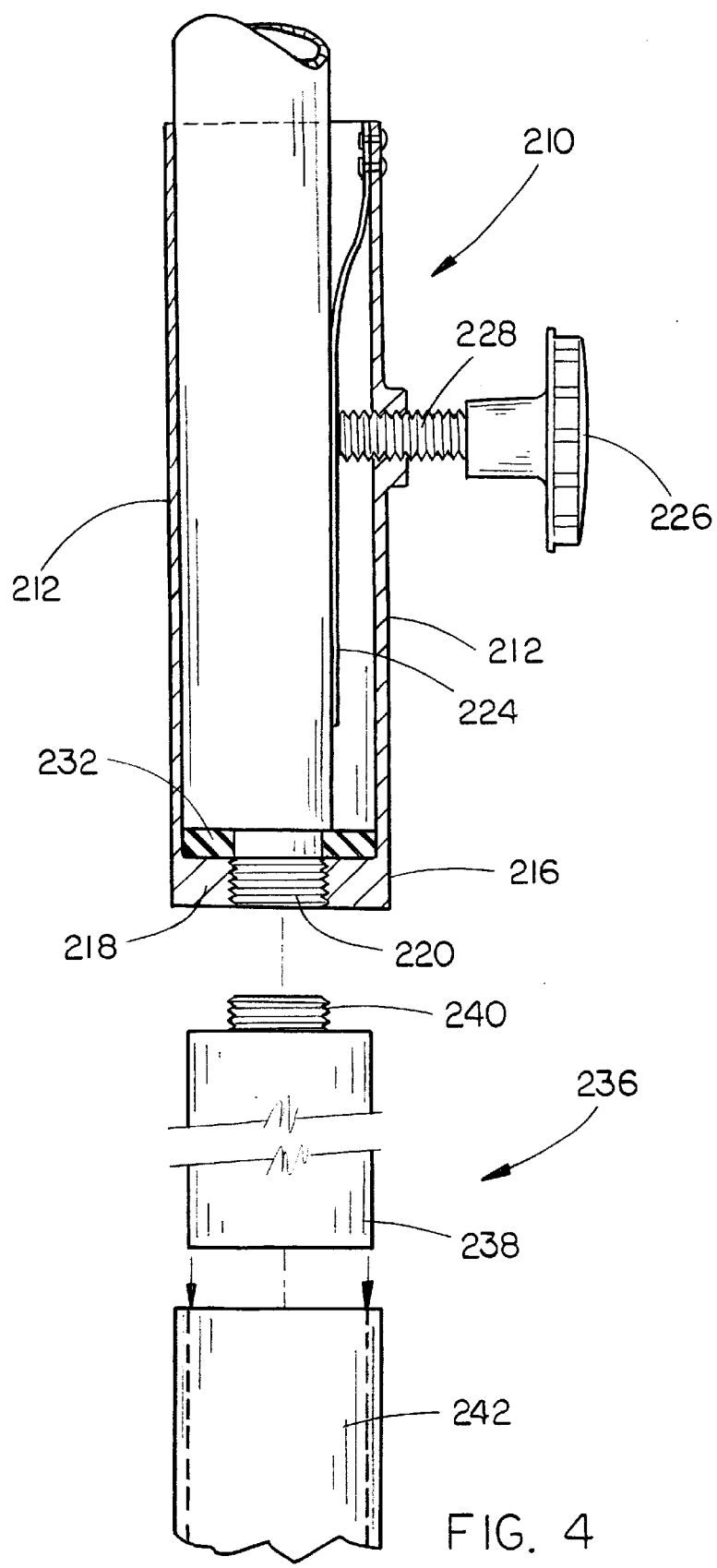
FIG. 4 is a vertical sectional view, exploded in part showing a third embodiment of the receiver tube.

Referring now to FIG. 4, a third embodiment of the receiver tube is designated generally at 210, and includes the same adjustment knob 226, shaft 228, guide strip 224, and cushion 232 within tube 212 as the first embodiment 10 of the invention. However, in this third embodiment of the invention, flange 218 in the lower end 216 of tube 212 is thicker, such that threads may be cut into the flange aperture 220. An adapter 236 is provided which includes a cylindrical body 238 with a threaded stub 240 formed on an upper end thereof for selective engagement with the threads in aperture 220. Adapter body 238 has a dimension specifically sized to fit within the receiver socket 242 of pre-existing equipment on gurneys, beds and/or wheelchairs. In this way, existing equipment may still utilize the adjustable receiver tube 210 of the present invention to receive IV poles of various diameters without requiring a custom fit pole.

Whereas the invention has been shown and described in connection with the preferred embodiments thereof, many modifications, substitutions and additions may be made which are within the intended broad scope of the appended claims.

I claim:

1. An adjustable receiver tube, comprising:
   an elongated, vertical tube having upper and lower ends and a cylindrical side wall with interior and exterior surfaces;
   an elongated, flat resilient strip, independent of the tube side wall, affixed at one end to the tube side wall interior surface adjacent the upper end, and extending downwardly within the tube adjacent and spaced from the tube interior surface to a lower free end;
   a stop formed in the lower end of the tube for supporting a pole in the tube; and
   means on the tube side wall for selectively biasing the free end of the strip inwardly within the tube.

2. The receiver tube of claim 1, further comprising a cushion mounted on the stop and formed of a material for frictionally engaging a pole journaled within the tube, to resist rotational and horizontal movement of the pole.

3. The receiver tube of claim 1, wherein said means for selectively biasing the strip includes:
   a threaded shaft with inward and outward ends, the inward end engaged in a threaded aperture formed through the tube side wall for selective inward and outward rotational advancement; and
   said threaded shaft located in alignment with the free end of the strip to bias the strip radially inwardly within the tube.

4. The receiver tube of claim 3, further comprising a knob mounted on the outward end of the shaft for selectively rotating the shaft.

5. The receiver tube of claim 4, further comprising a cushion mounted on the stop and formed of a material for frictionally engaging a pole journaled within the tube, to resist rotational and horizontal movement of the pole.

6. An adjustable receiver tube, comprising:
   an elongated, vertical tube having upper and lower ends and a cylindrical side wall with interior and exterior surfaces;
   an elongated, flat resilient strip affixed at one end to the tube side wall adjacent the upper end, and extending downwardly within the tube to a lower free end;
   said strip upper end being affixed to the tube interior surface, and formed of spring steel;
   a stop formed in the lower end of the tube for supporting a pole in the tube;
   means on the tube side wall for selectively biasing the free end of the strip inwardly within the tube;
   said means for selectively biasing the strip including:
      a threaded shaft with inward and outward ends, the inward end engaged in a threaded aperture for selective inward and outward rotational advancement; and
      said threaded shaft located in alignment with the free end of the strip to bias the strip radially inwardly within the tube;
   a knob mounted on the outward end of the shaft for selectively rotating the shaft;
   a cushion mounted on the stop and formed of a material for frictionally engaging a pole journaled within the tube, to resist rotational and horizontal movement of the pole;
   said stop including an annular flange extending radially inwardly from the tube side wall, said flange having an aperture formed therein to permit fluid flow therethrough.

7. The receiver tube of claim 6, wherein said cushion has an opening formed therein aligned with the flange aperture, for fluid flow therethrough.

8. The receiver tube of claim 7, wherein said aperture in said flange is threaded to receive a threaded stub on an adapter.

9. The receiver tube of claim 8, further comprising an elongated generally cylindrical adapter having a threaded stub projecting from an upper end thereof, the stub threaded into the flange aperture.

10. The receiver tube of claim 1, wherein said means for selectively biasing the strip includes:
   a threaded shaft with inward and outward ends, the inward end engaged in a threaded aperture for selective inward and outward rotational advancement; and
   said threaded shaft located in alignment with the free end of the strip to bias the strip radially inwardly within the tube.

11. An adjustable receiver tube, comprising:
   an elongated, vertical tube having upper and lower ends and a cylindrical side wall with interior and exterior surfaces;
   an elongated, flat resilient strip affixed at one end to the tube side wall adjacent the upper end, and extending downwardly within the tube to a lower free end;
   a stop formed in the lower end of the tube for supporting a pole in the tube;
   said stop including an annular flange extending radially inwardly from the tube side wall, said flange having an aperture formed therein to permit fluid flow therethrough.

12. The receiver tube of claim 11, wherein said aperture in said flange is threaded to receive a threaded stub on an adapter.

13. The receiver tube of claim 12, further comprising an elongated generally cylindrical adapter having a threaded stub projecting from an upper end thereof, the stub threaded into the flange aperture.

14. An adjustable receiver tube, comprising:
   an elongated, vertical first tube having upper and lower ends and a cylindrical side wall with interior and exterior surfaces;
   an elongated, flat resilient strip affixed at one end to the tube side wall adjacent the upper end, and extending downwardly within the tube to a lower free end;
   a stop formed in the lower end of the tube for supporting a pole in the tube;
   means on the tube side wall for selectively biasing the free end of the strip inwardly within the tube;
   a second elongated, vertical tube having an upper end connected to the first tube lower end, said tube coaxial with the first tube and having a lower end and a cylindrical side wall;
   an elongated, flat resilient strip affixed at one end to the second tube side wall adjacent the lower end and extending upwardly within the second tube to an upper free end; and
   means on the second tube side wall for selectively biasing the second tube strip free end inwardly within the second tube.

15. The receiver tube of claim 14, wherein said means for selectively biasing the second tube strip includes:
   a second threaded shaft with inward and outward ends, the inward end engaged in a threaded aperture for selective inward and outward rotational advancement; and
   said second threaded shaft located in alignment with the second strip free end to bias the strip radially inwardly within the second tube.

16. The receiver tube of claim 14, further comprising a cushion mounted in the second tube upper end, formed of a material for frictionally engaging a pole journaled within the second tube, to resist rotational and horizontal movement of the pole.

17. An adjustable receiver tube, comprising:
   an elongated, vertical tube having upper and lower ends and a cylindrical side wall with interior and exterior surfaces;
   an elongated, flat resilient strip affixed at one end to the tube side wall adjacent the upper end, and extending downwardly within the tube to a lower free end;
   a stop formed in the lower end of the tube for supporting a pole in the tube;
   means on the tube side wall for selectively biasing the free end of the strip inwardly within the tube;
   said stop including an annular flange extending radially inwardly from the tube side wall with a central threaded aperture therethrough; and
   an adapter removably connected to the threaded aperture, said adapter including an elongated body having a predetermined shape for slidable engagement within a socket having a predetermined shape.

18. The receiver tube of claim 17, wherein said adapter includes a threaded stub on an upper end, said stub engaged with the threaded aperture to removably secure the adapter to the receiver tube.

19. A receiver tube, comprising:
   an elongated vertical tube having upper and lower ends and a cylindrical side wall with interior and exterior surfaces;
   a first elongated, flat, resilient strip affixed at an upper end to the tube side wall upper end and extending downwardly within the tube to a lower free end;
   a second elongated, flat, resilient strip affixed at a lower end to the tube side wall lower end and extending upwardly within the tube to an upper free end;
   a stop formed within the tube between the free ends of the strips to prevent longitudinal movement of poles journaled through the tube ends beyond the stop;
   first means in the side wall for selectively biasing the first strip free end inwardly within the tube; and
   second means in the tube side wall for selectively biasing the second strip free end inwardly within the tube.

* * * * *